US009051245B2

(12) United States Patent
Kishi et al.

(10) Patent No.: US 9,051,245 B2
(45) Date of Patent: Jun. 9, 2015

(54) RESVERATROL POLYMERIZATION COMPOUND OR PHARMACEUTICALLY ACCEPTABLE SALT THEREOF

(75) Inventors: Akinobu Kishi, Yamatokooriyama (JP); Satoshi Doi, Yamatokooriyama (JP); Taiji Matsukawa, Yamatokooriyama (JP); Takeki Matsui, Yamatokooriyama (JP); Yasumasa Yamada, Yamatokooriyama (JP); Ichiro Yamada, Yamatokooriyama (JP)

(73) Assignee: UHA MIKAKUTO CO., LTD., Yamatokooriyama-shi (JP)

( * ) Notice: Subject to any disclaimer, the term of this patent is extended or adjusted under 35 U.S.C. 154(b) by 0 days.

(21) Appl. No.: 14/353,882

(22) PCT Filed: Oct. 27, 2011

(86) PCT No.: PCT/JP2011/074870
§ 371 (c)(1),
(2), (4) Date: Apr. 24, 2014

(87) PCT Pub. No.: WO2013/061455
PCT Pub. Date: May 2, 2013

(65) Prior Publication Data
US 2014/0288334 A1   Sep. 25, 2014

(51) Int. Cl.
C07C 39/23 (2006.01)
C07C 37/14 (2006.01)
(52) U.S. Cl.
CPC .............. C07C 39/23 (2013.01); C07C 37/14 (2013.01)
(58) Field of Classification Search
None
See application file for complete search history.

(56) References Cited

FOREIGN PATENT DOCUMENTS

| JP | H02-48533 | 2/1990 |
| JP | 2005-143377 A1 | 6/2005 |
| JP | 2009-173570 A1 | 8/2009 |
| JP | 2009-191049 A1 | 8/2009 |

OTHER PUBLICATIONS

Database CAPLUS on STN, Acc. No. 2007:898311, Wu et al., Journal of Asian Natural Products Research (2007), 9(5), pp. 471-477 (abstract).*
J. Baur, et al.; "Therapeutic potential of resveratrol: the in vivo evidence;" Nature Reviews|Drug Discovery; vol. 5; Jun. 2006; pp. 493-506 (14 Sheets).
M. Jang, et al.; "Cancer Chemopreventive Activity of Resveratrol, a Natural Product Derived from Grapes;" Science; vol. 275; Jan. 10, 1997; pp. 218-220 and cover sheet (4 Sheets).
J. Milne, et al.; "Small molecule activators of SIRT1 as therapeutics for the treatment of type 2 diabetes;" Nature; vol. 450; No. 29; 2007; pp. 712-716 (5 Sheets).
International Search Report for International Application No. PCT/JP2011/074870 dated Dec. 27, 2011.

* cited by examiner

*Primary Examiner* — Brian J Davis
(74) *Attorney, Agent, or Firm* — Kratz, Quintos & Hanson, LLP

(57) ABSTRACT

This invention relates to a resveratrol polymerization compound represented by Formula (1) (in which, in Formula (1), $R_1$ and $R_2$ represent —OH or Formula (2) and $R_1$ and $R_2$ are not the same) or a pharmaceutically acceptable salt thereof and an anticancer agent, an anticancer agent for oral cancer, an antioxidant, an antibacterial agent, a lipase inhibitor, an antiobesity agent, a therapeutic agent for skin diseases, a food, a pharmaceutical agent, a quasi drug, or a cosmetic containing one or more compounds selected from the group consisting of the resveratrol polymerization compound and the pharmaceutically acceptable salt thereof.

9 Claims, 1 Drawing Sheet

Chromatogram of resveratrol solution after reaction

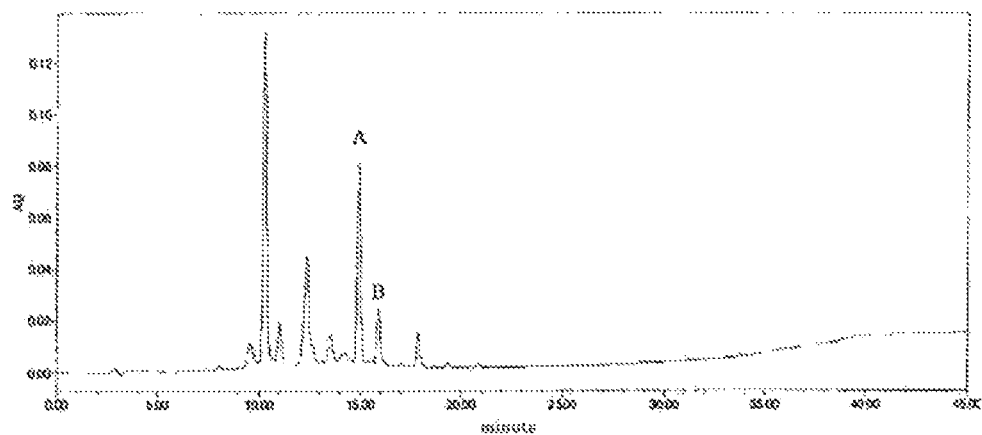
Fig. 1 Chromatogram of resveratrol solution after reaction
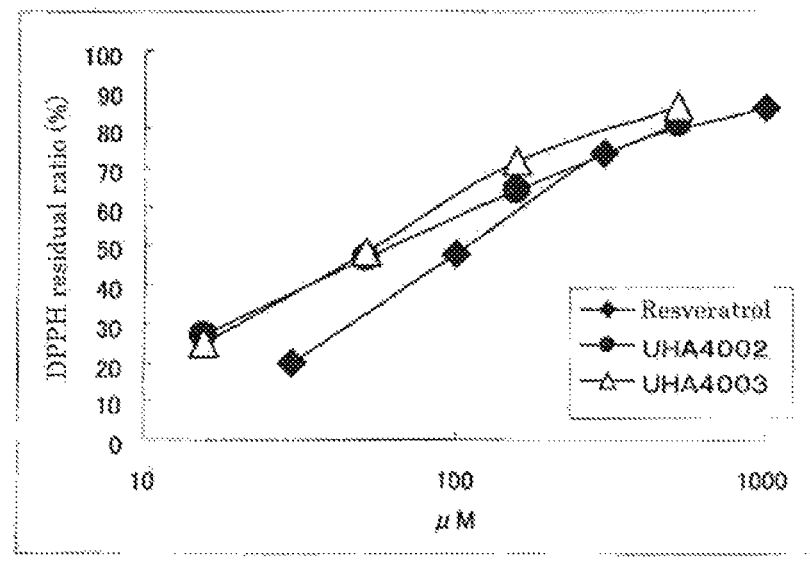
Fig. 2 DPPH radical elimination method of each compound

RESVERATROL POLYMERIZATION COMPOUND OR PHARMACEUTICALLY ACCEPTABLE SALT THEREOF

TECHNICAL FIELD

The present invention relates to a novel resveratrol polymerization compound or a pharmaceutically acceptable salt thereof and a method for manufacturing the same and relates to foods, pharmaceutical agents, quasi drugs, or cosmetics containing the resveratrol polymerization compound and the like.

BACKGROUND ART

It is known that the resveratrol which is a stilbene derivative contained in the grape pericarp is originally a compound having an antibacterial action and present as phytoalexin in which the grape protects oneself from germs and is contained in the grape pericarp regardless of a red type and a white type. It has become increasingly clear by the latest research that the resveratrol has useful effects also to mammals. It is considered that various kinds of bioactive functions including the antioxidation ability of the resveratrol are part of the reason of the useful bioactive effect of red wine which is referred to as a so-called "French paradox". Furthermore, it has become increasingly clear that the resveratrol has effects on a large number of diseases (Non-patent Document 1). As one of the effects, it has been clarified that the resveratrol has strong anticancer action (Non-patent Document 2). However, edible plants containing the resveratrol are extremely limited and limited to grapes, peanuts, and the like. In the grape, the resveratrol is contained in a high proportion particularly in the grape pericarp but the content is very low and is said to be as low as about 50 to 100 μg/g (Non-patent Document 2).

Then, an approach of increasing the resveratrol concentration in foods has also been performed, and a food obtained by increasing the resveratrol concentration by ultraviolet ray exposure to obtain a resveratrol containing extract, and then adding the extract to a food has been proposed (Patent Document 1). Moreover, as a technique of increasing the intestinal tract absorption efficiency of the resveratrol, an intestinal tract absorption accelerator has also been proposed (Patent Document 2). Thus, the resveratrol is a compound which has extremely excellent properties, such as an anticancer action, an antioxidant action, and an antibacterial action. However, since the resveratrol is a rare component, the cost of products thereof becomes high. Therefore, the resveratrol is commercially available as a supplement and the like but it is hard to be said that the resveratrol fully pervades the society.

On the other hand, as derivatives of the resveratrol, a large number of polymers of the resveratrol have been reported as natural substances, such as s-viniferin (dimer), α-viniferin (trimer), and vaticanol C (tetramer), for example. All the substances are natural rare components similarly as the resveratrol and a technique of supplying these derivatives of the resveratrol in a sufficient amount is not known.

Then, an attempt of producing novel compounds by chemical synthesis referring to the action mechanism of the resveratrol has been made in the pharmaceutical agent field (Non-patent Document 3). However, the novel compounds are development targets mainly as pharmaceutical agents and still have a large number of problems in term of safety.

CITATION LIST

Patent Literatures

Patent Document 1: JP-A No. 2005-143377
Patent Document 2: JP-A No. 2009-173570
Non-patent Document 1: Drug Discovery, 5, 493-506 (2006)
Non-patent Document 2: Science. Vol. 275 (10) 218-220 (1997)
Non-patent Document 3: Nature. Vol. 450 (29) 712-716 (2007)

SUMMARY OF INVENTION

Technical Problem

In view of the above-described circumstance relating to the resveratrol, the present inventors have conducted extensive research of searching a resveratrol derivative having stronger bioactivity and establishing a method for manufacturing the same. As a result, unexpectedly, the present inventors have succeeded in manufacturing a novel resveratrol polymerization compound having more excellent bioactivity as compared with resveratrol and known resveratrol derivatives by a simple and safe method of heat-treating the resveratrol under alkaline conditions, and thus have accomplished the present invention.

Therefore, it is an object of the present invention to provide a novel resveratrol polymerization compound having stronger bioactivity than that of the resveratrol and further provide a method for generating the resveratrol polymerization compound with good efficiency and safety.

Moreover, it is an object of the present invention to provide an anticancer agent, an anticancer agent for oral cancer, an antioxidant, an antibacterial agent, a lipase inhibitor, an anti-obesity agent, a therapeutic agent for skin diseases, a food, a pharmaceutical agent, a quasi drug, or a cosmetic containing the resveratrol polymerization compound.

Solution to Problem

The gist of the present invention is as follows:

[1] A resveratrol polymerization compound represented by Formula (1),

[C. 1]

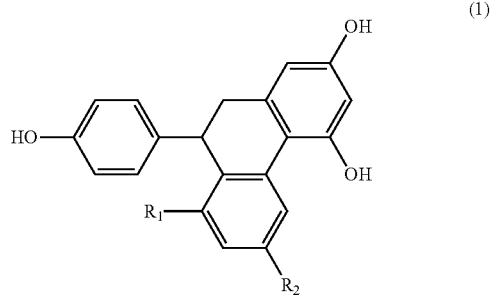

(wherein, in Formula (1), $R_1$ and $R_2$ independently represent —OH or Formula (2),

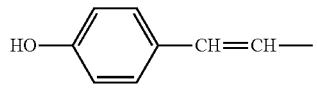

and $R_1$ and $R_2$ are not the same) or a pharmaceutically acceptable salt thereof (hereinafter referred to as resveratrol polymerization compounds),

[2] An anticancer agent containing one or more kinds of the resveratrol polymerization compounds according to [1],

[3] An antioxidant containing one or more kinds of the resveratrol polymerization compounds according to [1],

[4] An antibacterial agent containing one or more kinds of the resveratrol polymerization compounds according to [1],

[5] An anticancer agent for oral cancer containing one or more kinds of compounds selected from the group consisting of the resveratrol polymerization compound and the pharmaceutically acceptable salt thereof according to [1],

[6] A lipase inhibitor containing one or more kinds of compounds selected from the group consisting of the resveratrol polymerization compound and the pharmaceutically acceptable salt thereof according to [1],

[7] An antiobesity agent containing one or more kinds of compounds selected from the group consisting of the resveratrol polymerization compound and the pharmaceutically acceptable salt thereof according to [1],

[8] A therapeutic agent for skin diseases containing one or more kinds of compounds selected from the group consisting of the resveratrol polymerization compound and the pharmaceutically acceptable salt thereof according to [1],

[9] A food, a pharmaceutical agent, a quasi drug, or a cosmetic containing one or more kinds of the resveratrol polymerization compounds according to [1], and

[10] A method for manufacturing the resveratrol polymerization compound or a pharmaceutically acceptable salt thereof according to [1], including a process of heat treating resveratrol under alkaline conditions.

Advantageous Effects of Invention

The resveratrol polymerization compounds of the present invention are excellent in bioactivities such as anticancer activity, anticancer activity to oral cancer, antioxidation activity, antibacterial activity, and lipase inhibition activity as compared with resveratrol, and therefore are useful as active components of a novel anticancer agent, an anticancer agent for oral cancer, an antioxidant, an antibacterial agent, a lipase inhibitor, an antiobesity agent, a therapeutic agent for skin diseases, and the like.

Moreover, in addition to the fact that the resveratrol polymerization compounds of the present invention are excellent in the above-described bioactivities, the resveratrol polymerization compounds of the present invention are excellent also in safety because the resveratrol which is the raw material is derived from foods, and therefore the resveratrol polymerization compounds of the present invention can be compounded into foods, pharmaceutical agents, quasi drugs, or cosmetics.

BRIEF DESCRIPTION OF THE DRAWINGS

FIG. 1 shows a chromatogram of a resveratrol solution after reaction obtained in Example 1, in which the peaks of main compounds are shown by A and B and the peak of A is a peak containing UHA4002 and the peak of B is a peak containing UHA4003.

FIG. 2 shows a graph showing the results obtained by a DPPH radical elimination method of Example 2.

In FIG. 2, the vertical axis represents a DPPH radical residual ratio and the horizontal axis represents the concentration of each sample.

DESCRIPTION OF EMBODIMENTS

Hereinafter, the present invention is described in detail.

The present invention is a dimer of resveratrol and is a resveratrol polymerization compound represented by Formula (1):

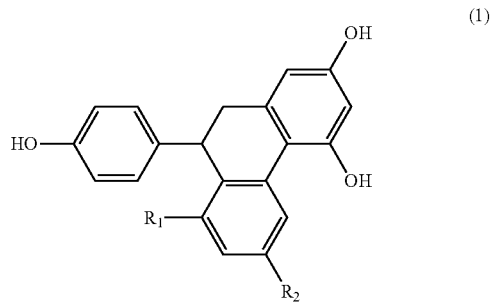

(wherein, in Formula (1), $R_1$ and $R_2$ represent —OH or

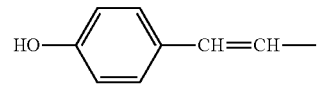

and $R_1$ and $R_2$ are not the same) or a pharmaceutically acceptable salt thereof.

In the resveratrol polymerization compound, a carbon-carbon double bond may be trans or cis and contains a mixture of a cis isomer and a trans isomer.

Examples of the pharmaceutically acceptable salt of the resveratrol polymerization compound include, for example, alkaline metal salts such as lithium salt, sodium salt, and potassium salt; alkaline earth metal salts such as magnesium salt, calcium salt, and barium salt; aluminum salt; metal hydroxide salts such as aluminum hydroxide salt; amine salts such as alkyl amine salt, dialkyl amine salt, trialkyl amine salt, alkylene diamine salt, cycloalkyl amine salt, aryl amine salt, aralkyl amine salt, and heterocyclic amine salt; amino acid salts such as α-amino acid salt and ω-amino acid salt; peptide salt or a primary, secondary, tertiary, or quaternary amine salt derived from the same, and the like. These pharmaceutically acceptable salts can be used singly or as a mixture of two or more kinds thereof.

The resveratrol polymerization compounds of the present invention having the above-described structure can be gradually chemically synthesized from a plurality of low molecular compounds in accordance with a known method in the relating technical field but the reaction process becomes complicated and a reagent and a process harmful to a human body are required. According to the chemical synthesis method, for the purpose of removing impurities in order to increase the reaction efficiency, it is required to completely refine the resveratrol polymerization compounds. Therefore, the chemical synthesis method is unsuitable for industrially manufacturing the resveratrol polymerization compound.

Then, the present inventors have extensively examined methods other than the chemical synthesis method and, as a result, found that, by alkali treating resveratrol under heating, the resveratrol polymerization compounds can be efficiently and safely manufactured without requiring harmful reagent and process. A manufacturing method of the present invention is specifically described below.

In the manufacturing method of the present invention, resveratrol is used as a precursor. In the resveratrol, structural isomers of a trans isomer and a cis isomer are present and the transformation of the trans isomer and the cis isomer occurs by heating or ultraviolet rays. Therefore, as the resveratrol for use in the present invention, any one of the trans isomer, the cis isomer, and a mixture of the trans isomer and the cis isomer may be acceptable. The resveratrol may be a naturally derived substance which is extracted and purified from the grape pericarp or a chemical product which is chemically synthesized and has high purity. In the case of using the naturally derived resveratrol, the resveratrol is not required to be completely purified and may be a mixture because a subsequent desired reaction proceeds, and then the resveratrol polymerization compounds of the present invention are finally obtained. Moreover, the resveratrol also includes derivatives such as salt, ether, and ester. According to the manufacturing method of the present invention, these derivatives can also be used as the raw material.

From the viewpoint of the recovery, a mixture containing the same in a proportion of 5% by weight or more in terms of resveratrol is desirable as the raw material.

According to the manufacturing method of the present invention, a pure article of resveratrol or a resveratrol containing mixture is first dissolved in a suitable solvent. In this case, when the solvent contains only water, the solubility of the resveratrol is remarkably low, and therefore the resveratrol may be dissolved in a mixed liquid of water and an organic solvent or only in an organic solvent. The compounding ratio of water and the organic solvent and the type of the organic solvent are not particularly limited and may be selected in such a manner that the resveratrol is sufficiently dissolved. In particular, it is preferable in terms of safety and cost to use a solvent containing only methanol or ethanol, a mixed liquid of water and methanol, or a mixed liquid of water and ethanol. When used for foods without sufficiently performing final purification, the use of ethanol or hydrous ethanol is desirable in terms of safety and laws and regulations. The concentration of the resveratrol in the resveratrol containing solution to be obtained is not limited. There is a merit that when the concentration is higher, the consumption amount of the solvent is small. Therefore, the concentration is preferably around a concentration at which the resveratrol is saturated in each solvent. The resveratrol may not be completely dissolved in the solution before a reaction.

Next, the resveratrol containing solution is adjusted to be alkaline. As the adjustment method, the resveratrol containing solution is prepared, and then an alkalizing agent may be added to adjust the pH or the pH of the solvent may be adjusted beforehand when preparing the resveratrol containing solution described above, for example. The pH of the resveratrol containing solution when starting the reaction is preferably 8.0 or more because the reaction described below efficiently proceeds. When the pH exceeds 13.0, another reaction and decomposition of the target compound occur simultaneously with the reaction, so that the recovery amount of the final resveratrol polymerization compounds decreases. Therefore, the pH when starting the reaction is preferably 8.0 to 13.0.

The alkalizing agent is not particularly limited and is preferably sodium hydroxide, potassium hydroxide, and sodium hydrogencarbonate in terms of safety, efficiency, and cost. When a case where the pH change in the reaction is suppressed as much as possible arises, a buffer solution may be used but the technique is not always required.

Next, the resveratrol containing solution adjusted to be alkaline is heated. This heating performs a generation reaction of the resveratrol polymerization compounds. In order to efficiently advance the reaction, the heating temperature of the resveratrol containing solution is preferably adjusted to 110° C. or higher. Considering the boiling point of the solvent to be used, it is preferable to perform pressurization and heating. It is preferable to perform the heating in such a manner that the solution temperature at least partially reaches 110° C. or higher by, for example, placing the resveratrol containing solution in an open container, and then heating the container at a high temperature exceeding the boiling point of the solvent, placing the resveratrol containing solution in an airtight container, and then heating the container, performing pressurization and heating using a retort apparatus or an autoclave, and the like. In terms of the recovery efficiency, the solution temperature more preferably uniformly reaches 120 to 180° C. The heating time is not limited similarly as the heating temperature and the heating time conditions may be set in such a manner that the target reaction efficiently proceeds. In particular, the heating time depends on the balance with the heating temperature and is preferably set to heating time in accordance with the heating temperature. For example, when performing the heating around 130° C., the heating time is preferably 5 minutes to 24 hours. The heating may be performed once or may be repeatedly performed in a plurality of steps. When performing the heating in a plurality of steps, it is preferable to perform the heating by further adding a solvent.

The completion of the generation reaction of the resveratrol polymerization compounds by the heating may be judged by confirming the generation amount by componential analysis by HPLC, for example.

In the reaction liquid to be obtained, as the resveratrol polymerization compound of the present invention, a compound 1 represented by Formula (2):

[C. 5]

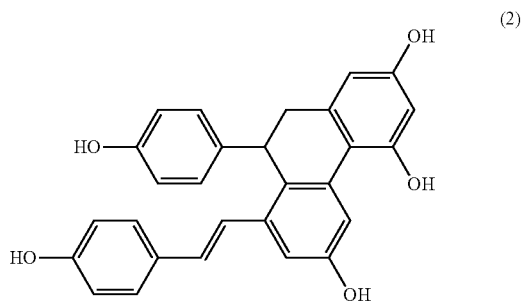

(2)

and a compound 2 represented by Formula (3) are present as a mixture.

[C. 6]

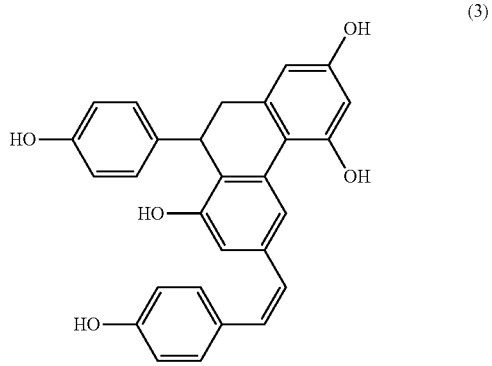

(3)

When the phenolic polymerization compound is manufactured only using safe raw materials, it is possible to use the same in the state of the mixture for foods, pharmaceutical agents, quasi drugs, cosmetics, and the like. For example, when naturally derived resveratrol is dissolved in a hydrous ethanol solvent, the pH is adjusted with sodium hydroxide or sodium hydrogencarbonate in such a manner that the solution becomes alkaline, and then a heating reaction is performed, a liquid reactant to be obtained can be used, as it is, as one of the food raw materials.

When an improvement of flavor and higher functionality are desired, a pure article of the resveratrol polymerization compound can be obtained by condensing the reactant to increase the concentration of the resveratrol polymerization compound or purifying the reactant. The concentration and purification can be carried out by known methods. For example, the resveratrol polymerization compound can be condensed by performing extraction by a solvent extraction method with chloroform, ethyl acetate, ethanol, or methanol, a supercritical extraction method with carbon dioxide, or the like. Moreover, the concentration and the purification can also be performed utilizing column chromatography. To the concentration and the purification, a recrystallizing method or a membrane treatment method with an ultrafiltration membrane or the like, is also applicable.

When isolating the compound 1 represented by Formula (2) and the compound 2 represented by Formula (3) from the reactant and collecting the same, column chromatography, high performance liquid chromatography (HPLC), and the like may be used.

The resveratrol polymerization compound in a powder state can be obtained by subjecting the concentrate and the purified substance to drying under reduced pressure or freeze drying to remove the solvent as required.

The resveratrol polymerization compounds of the present invention obtained as described above all have excellent anticancer activity, anticancer activity to oral cancer, antioxidation activity, antibacterial activity, and lipase inhibition activity as compared with resveratrol or known resveratrol polymerization compounds. Therefore, an anticancer agent, an anticancer agent for oral cancer, an antioxidant, an antibacterial agent, a lipase inhibitor, an antiobesity agent, and a therapeutic agent for skin diseases containing the resveratrol polymerization compounds as the active component can be provided.

The anticancer agent, the anticancer agent for oral cancer, the antioxidant, the antibacterial agent, the lipase inhibitor, the antiobesity agent, and the therapeutic agent for skin diseases may contain either one singly or both of the compound 1 represented by Formula (2) and the compound 2 represented by Formula (3). Other active ingredients may be contained in combination.

Since the two kinds of compounds are similar to each other in the bioactivities and the physicochemical properties, the compounds can be used for the same intended use or with the same amount.

Further effects and efficacy of the compound obtained by the present invention can be used in the range which can be analogized from the obtained bioactive data.

Since the safety of the resveratrol which is the raw material is confirmed and the safety of known resveratrol polymerization compounds is also confirmed, the safety of the resveratrol polymerization compounds of the present invention is similarly excellent.

The resveratrol polymerization compounds of the present invention can be compounded into foods, pharmaceutical agents, quasi drugs, cosmetics, and the like for use.

The foods may be in any form such as beverages, alcoholic beverages, jellies, confectioneries, and the like, for example. Among the confectionaries, a hard candy, a soft candy, a gummi candy, a tablet, and the like which are excellent in storageability or portability from the capacity and the like are mentioned but the confectionaries are not particularly limited thereto. Moreover, in terms of reinforcing the effects of the resveratrol, by adding the compound to wine, a novel wine in which the health function effects of the wine is further enhanced can be obtained. Foods and beverages having both palatability and the health function effect is a field with very high social needs and can satisfy the needs. The foods further include functional foods, health foods, health-oriented foods, and the like.

The pharmaceutical agents include solid preparations such as powder agents, tablets, pills, capsule agents, fine grain agents, and granule agents; liquid agents such as water agents, suspension agents, and emulsion agents; gel agents, and the like. The tablets, pills, granule agents, and granules in capsule agents containing granules can be sugar-coated with sugars such as sucrose, and sugar alcohols such as maltitol, coated with gelatin, hydroxypropyl cellulose, hydroxypropyl methylcellulose, and the like as required. Or, the tablets, pills, granule agents, and granules in capsule agents containing granules may be covered with a film of a gastric-soluble substance or an enteric-soluble substance. The pharmaceutical agents mentioned above can be also subjected to known solubilization treatment in order to increase the solubility of the preparations. The agents may be compounded into injection agents and drop agents for use based on a usual method.

The quasi drugs include quasi drugs for use in the oral, such as toothpastes, mouthwashes, mouse rinses, and revitalizing beverages for protection against infectious diseases.

The cosmetics include lotions, milky lotions, creams, facial mask agents, finishing cosmetics, hair care products, face washing agents, bath agents, antiperspirants, and the like. With respect to these cosmetics, beauty effects are expected from the antioxidation effect and can be utilized for protection against bacteria from the antibacterial effect.

When preparing foods, pharmaceutical agents, quasi drugs, or cosmetics using the resveratrol polymerization compounds of the present invention, the components generally used for foods, pharmaceutical agents, quasi drugs, or cosmetics can be arbitrarily compounded as appropriate in the range where the effects of the present invention are not impaired.

For example, in the case of foods, the resveratrol polymerization compounds of the present invention can be combined with raw materials or materials usually compounded into foods such as water, alcohol, starch, protein, fiber, sugar, lipid, vitamin, mineral, a flavoring agent, a colorant, a sweetener, a seasoning, a stabilizer, and an antiseptic agent.

In the case of cosmetics and quasi drugs, the resveratrol polymerization compounds of the present invention can be combined with a main agent, a base material, a surfactant, a foaming agent, a moisturizing agent, a thickening agent, a clearing agent, a flavoring agent, a colorant, a stabilizer, an antiseptic agent, a disinfectant, and the like. In the case of cosmetics, the cosmetics can be prepared into the form of a liquid, an ointment, a final form which can be spray ejected, and the like based on a usual method. To these cosmetics, other components can be compounded according to the intended use. In the case of a milky lotion, for example, hydrophilic bases such as propylene glycol, hydrophobic bases such as vaseline and beeswax, alcohols such as ethyl alcohol, emulsifiers such as fatty acid monoglycerides and sorbitan fatty acid esters, pigments, perfumes, and, as required, nutrients, humectants, UV absorbers, or the like in accordance with the intended use can be compounded.

In the case of pharmaceutical agents or quasi drugs, the resveratrol polymerization compounds of the present invention can be combined with a carrier, a diluent base, a dilution agent, and a stabilizer.

When adding the resveratrol polymerization compounds of the present invention to foods, it is usually preferable to add the same into the foods in a proportion of 0.001 to 20% by weight.

When the resveratrol polymerization compounds of the present invention are used for medical application, the intake, for example, is not particularly limited insofar as a desired improvement effect, a desired medical treatment effect, or a desired preventive effect is obtained and is usually selected as appropriate according to the aspect thereof, the age, sex, physical constitution, other conditions of patients, and the kind and extent of diseases, and the like. The intake may be about 0.1 mg to about 1,000 mg per day and can be divided into 1 to 4 doses per day.

When adding the resveratrol polymerization compounds of the present invention to quasi drugs, it is usually preferable to add the same into the quasi drugs in a proportion of 0.001 to 30% by weight.

When using the resveratrol polymerization compounds of the present invention as cosmetics, it is preferable to add the same in such a manner that the concentration is 0.1 ppm to 2000 ppm in the cosmetics.

Moreover, since the resveratrol polymerization compounds of the present invention are excellent in safety, the resveratrol polymerization compounds of the present invention may be used not only for human beings and may be compounded into therapeutic agents or feed for nonhuman animals, for example, mammals such as rats, mice, guinea pigs, rabbits, sheep, pigs, cows, horses, cats, dogs, apes, and chimpanzees, birds, amphibians, and reptiles. The feed includes, for example, cattle feeds for sheep, pigs, cows, horses, chickens, and the like, feeds for small animals for rabbits, rats, mice, and the like, feeds for fish and shellfishes for eels, sea breams, yellowtails, shrimps, and the like, and pet foods for dogs, cats, caged little birds, squirrels, and the like.

In particular, when the bioactive field of the resveratrol polymerization compounds of the present invention is taken into consideration, it is preferable to use the same in maintenance and improvement of health such as cancer prevention and cancer treatment, and protection against lifestyle-related diseases and infectious diseases and treatment thereof, and further in the field of recovery from diseases.

Moreover, it is also suitable to use the resveratrol polymerization compounds of the present invention in the quality control field such as antioxidation and prevention of microbial contamination of foods, cosmetics, and the like.

Next, the present invention is described in detail based on Examples but the present invention is not limited only to the Examples.

EXAMPLES

Example 1

Generation of Resveratrol Polymerization Compound 700 mg of trans-resveratrol (manufactured by Tokyo Chemical Industry Co., Ltd.) was dissolved in 14 ml of ethanol, and then 14 mL of a 2.5% $NaHCO_3$ aqueous solution was added thereto to obtain a resveratrol containing solution (pH 9.9). The resveratrol containing solution was heated at 130° C. for 20 minutes in an autoclave ("SANYO LABO AUTOCLAVE" manufactured by SANYO Electric Co., Ltd., which was used in the following Examples). Subsequently, 14 ml of ethanol and 14 mL of a 5.0% $NaHCO_3$ aqueous solution were added to the reaction solution obtained by the first autoclave treatment, and then heated again at 130° C. for 20 minutes in the autoclave. Then, 1 mL of the obtained reaction solution was diluted with methanol in a measuring cylinder to 50 mL, and then 10 L, thereof was analyzed by HPLC.

The HPLC analysis was performed under the following conditions.

Column: Negative-phase column "Develosil (Registered Trademark) C-30-UG-5" (4.6 mmi·d.×250 mm)

Mobile phase: A . . . $H_2O$ (0.1% trifluoroacetic acid (TFA)), B . . . Acetonitrile (0.1% TFA)

Flow velocity: 1 mL/min

Pouring: 10 µL

Detection: 254 nm

Gradient (% by capacity): From 80% A/20% B to 20% A/80% B for 30 minutes, From 20% A/80% B to 100% B for 5 minutes, 100% B for 10 minutes (all straight line)

The obtained chromatograms are shown in FIG. 1. The peaks of the main compounds were shown by A and B.

Example 2

Isolation and Structural Determination of Resveratrol Polymerization Compound

The compounds contained in the peaks A and B were purified by fractionation HPLC from the reactant obtained in Example 1, and then dried, whereby 66.5 mg of a phenolic polymerization compound (hereinafter referred to as UHA4002) of light brown powder was obtained from the peak A and 31.5 mg of a novel compound (hereinafter referred to as UHA4003) of light brown powder was obtained from the peak B. All the compounds had a form of light brown powder.

Subsequently, when the molecular weights of UHA4002 and 4003 were measured by a high resolution FAB-MS (Fast Atom Bombardment Mass Spectrometer), the measured values of the compounds were 439.4803 and 439.4765, respectively. The following molecular formula was obtained from the comparison with the theoretical values.

Theoretical value $C_{28}H_{23}O_5$ $(M+H)^+$: 439.4792
Molecular Formula $C_{28}H_{22}O_5$ Next, the UHA4002 and 4003 were subjected to nuclear magnetic resonance (NMR) measurement. Then, it was confirmed that the UHA4002 had the structure of the compound 1 represented by Formula (2) and the UHA4003 had the structure of the compound 2 represented by Formula (3) from the analysis of $^1$H-NMR, $^{13}$C-NMR, and various two-dimensional NMR data. Thus, it was shown that the compound 1 represented by Formula (2) and the compound 2 represented by Formula (3) can be efficiently produced by the method of the present invention.

With respect to the NMR measured values, when the UHA4002 is as follows, and

[C. 7]

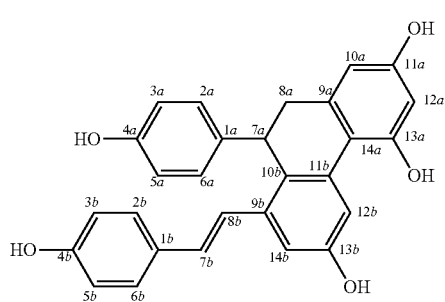

(2)

the UHA4003 is as follows,

[C. 8]

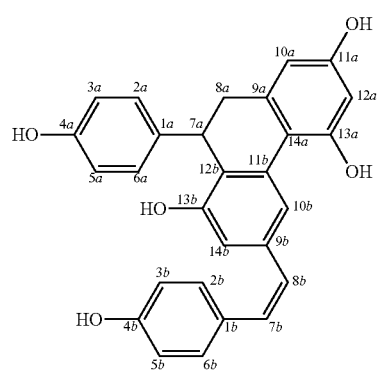

(3)

the $^1$H nuclear magnetic resonance spectrum and the $^{13}$C nuclear magnetic resonance spectrum of each compound are shown in Table 1.

The values were δ and ppm and were measured with a solvent of DMSO-de.

TABLE 1

| | $^1$H nuclear magnetic resonance spectrum and $^{13}$C nuclear magnetic resonance spectrum of each compound | | | |
|---|---|---|---|---|
| | UHA4002 (Compound 1) | | UHA4003 (Compound 2) | |
| | $^{13}$C | $^1$H | $^{13}$C | $^1$H |
| 1a | 133.1 | | 133.2 | |
| 2a, 6a | 115.6 | 6.71 (2H, d, J = 8.7 Hz) | 128.5 | 6.77 (2H, d, J = 8.5 Hz) |
| 3a, 5a | 114.6 | 6.49 (2H, d, J = 8.7 Hz) | 114.3 | 6.46 (2H, d, J = 8.5 Hz) |
| 4a | 155.1 | | 155.0 | |
| 7a | 37.3 | 4.36 (1H, d, J = 4.0 Hz) | 34.0 | 4.37 (1H, d, J = 4.2 Hz) |
| 8a | 37.8 | 2.85 (1H, d, J = 13.2 Hz) 3.00 (1H, d, J = 4.0, 13.2 Hz) | 37.0 | 2.85 (1H, d, J = 13.0 Hz) 2.97 (1H, d, J = 4.2, 13.0 Hz) |
| 9a | 137.9 | | 138.2 | |
| 10a | 107.4 | 5.96 (1H, s) | 107.4 | 5.99 (1H, s) |
| 11a | 156.8 | | 156.9 | |
| 12a | 102.0 | 6.22 (1H, s) | 102.0 | 6.22 (1H, s) |
| 13a | 155.6 | | 155.6 | |
| 14a | 113.0 | | 112.8 | |
| 1b | 128.1 | | 134.6 | |
| 2b, 6b | 127.5 | 7.24 (2H, d, J = 8.7 Hz) | 115.7 | 6.74 (2H, d, J = 8.7 Hz) |
| 3b, 5b | 128.3 | 6.76 (2H, d, J = 8.7 Hz) | 128.2 | 7.38 (2H, d, J = 8.7 Hz) |
| 4b | 157.4 | | 157.2 | |
| 7b | 129.3 | 6.87 (1H, d, J = 16.0 Hz) | 127.5 | 6.88 (1H, br s) |
| 8b | 123.0 | 7.00 (1H, d, J = 16.0 Hz) | 126.8 | 6.88 (1H, br s) |
| 9b | 135.6 | | 135.5 | |
| 10b | 127.3 | | 109.6 | 6.82 (1H, s) |
| 11b | 134.7 | | 153.1 | |
| 12b | 114.5 | 7.84 (1H, s) | 126.0 | |
| 13b | 155.0 | | 134.7 | |
| 14b | 108.9 | 6.86 (1H, s) | 117.5 | 8.10 (1H, s) |

The physicochemical properties of the UHA4002 and UHA4003 were as follows.

(Property)
Light brown powder
(Solubility)
Water: Poorly soluble
Methanol: Soluble
Ethanol: Soluble
DMSO: Soluble
Chloroform: Poorly soluble
Ethyl acetate: Poorly soluble

Example 3

Anticancer Action

Next, in order to see the effect of each compound to cancer cells, the cancer cell growth inhibitory action using HL-60 cells (human myeloid leukemia cells) was tested.

As culturing of cells, one in which 4 mM glutamine (L-glutamine, Sigma-Aldrich, "G8540-100G") and 10% FBS (fetal bovine serum, Biological Industries, "04-001-1A") were added to a high nutrient medium RPMI-1690 (Sigma-Aldrich, "R0883") was used as a culture solution, and then subculture was performed. For a test, a 96-well plate for cell culture (Corning, "3595") was used. The number of cells was adjusted on the test day in such a manner that the number of the HL-60 cells was $5 \times 10^5$ cell/mL, and then seeded in the 96-well plate with 100 µL/well.

As the samples, four kinds of samples of trans-resveratrol, ε-viniferin (Wako Pure Chemical Industries) which is a natural resveratrol dimer, and the UHA4002 and 4003 which are the articles of the present invention were used. For the preparation of the samples, each compound was dissolved with DMSO (dimethylsulfoxide, Wako Pure Chemical Industries, "046-21981"), and then the final concentration in the culture solution of the HL-60 cells of the samples was adjusted to be 10 µM, 30 µM, 100 µM, and 300 µM, respectively, and then the test was started.

For the detection of the cell growth inhibitory effect, the detection was performed by a MTT method using "Cell counting kit-8" (Dojin Chemical Laboratory, "347-07621"). More specifically, 24 hours after starting the test, 10 µL of the detection liquid of the cell counting kit-8 was added to each well, and then sufficiently stirred. Thereafter, a shading reaction was performed, the absorbance at 450 nm was measured using a plate reader (Biorad Laboratories, "BIO-RAD Model 680"), and then the obtained data were treated. The cell viability is a value obtained by calculation under the conditions where the number of survival cells of the cells treated with the culture solution to which DMSO was added was 100% and the number of survival cells of the cells under the concentration of each compound was defined as a relative value. From the relationship between each sample concentration and the cell viability, the concentration $IC_{50}$ (50% inhibitory concentration) which inhibits the cell growth by 50% was calculated. The results are shown in Table 2.

The results of Table 2 clarified that, in both the UHA4002 and 4003, the $IC_{50}$ was notably lower than that of resveratrol and E-viniferin and, more specifically, the effect of inhibiting the growth of the HL-60 cells of the UHA4002 and 4003 is twice or higher than that of resveratrol and E-viniferin.

TABLE 2

Cell growth inhibition ability of each compound ($IC_{50}$)

|  | µM |
|---|---|
| Resveratrol | 80 |
| ε-viniferin | 60 |
| UHA 4002 | 30 |
| UHA 4003 | 30 |

Example 4

Antioxidation Action

A test of the antioxidation effect of the UHA4002 and 4003 was performed. The test was performed by adopting a DPPH (1,1-diphenyl-2-picrylhydrazyl) radical elimination method. A technique thereof is mentioned below.

About the main experiment method of the DPPH radical elimination method, the test was advanced with reference to a technique described in "Methods for Functional Food Analysis" (Published by Korin Publishing Co., Ltd., edited by Kazuki SHINOHARA, Tateo SUZUKI, and Shuichi KAMINOGAWA, 2000). For the samples, UHA4002, 4003, and resveratrol were used and the final concentration was adjusted at 4 points in the range of 30 µM to 1000 µM. The DPPH reaction liquid was adjusted in such a manner as to be 400 µM DPPH (Sigma-Aldrich "D9132"), 50 mM MES (2-morpholinoethanesulphonic acid, Dojindo Laboratories, "345-01625"), and 75% ethanol. The reaction was performed in a 96-well plate (As One, "1-6776-03"), and 100 µL of the samples and 100 µL of the DPPH reaction liquid were placed, and then mixed. The mixture was allowed to stand still in a shading state for 20 minutes, and then each absorbance at 520 nm was measured with a plate reader.

The obtained results are shown in FIG. 2. In the UHA4002 and 4003, the radical residual ratio was lower than that of resveratrol at a low concentration, and more specifically the antioxidant action was higher than that of resveratrol. Table 3 shows the $IC_{50}$ of each compound. The $IC_{50}$ refers to a concentration of each sample which is considered to have an ability of eliminating 50% DPPH radical. It is found that the UHA4002 and 4003 have a strong antioxdation activity as high as twice that of resveratrol.

TABLE 3

Radical capturing ability of each compound ($IC_{50}$)

|  | µM |
|---|---|
| Resveratrol | 100 |
| UHA 4002 | 50 |
| UHA 4003 | 50 |

Example 5

Antibacterial Action

An assay was performed by a paper disc method for the purpose of confirming the antibacterial action of the UHA4002 and 4003. The paper disc method is a known technique capable of easily investigating the antibacterial activity of a test substance by creating each inhibition zone of the test substance.

The assay was performed using, as a fungus body, *Bacillus subtilis* (NBRC 3134) purchased from National Institute of Technology and Evaluation Biological Resource Center NBRC. For the raise of a fungus body and a culture method thereof, No. 702 which is a culture solution specified by NBRC was adjusted and used. The culture was performed at 37° C.

The experiment method of the paper disc method ((Agar) culture solution, Culture method, Test preparation, Test method) was performed in accordance with a BSAC standardization disc sensitivity test method (8th edition).

For the samples, resveratrol and the UHA4002 and 4003 were used and each adjusted using DMSO in such a manner as to be 50 mM, 10 mM, 5 mM, and 1 mM. As a positive control, chloramphenicol (Wako Pure Chemical Industries, "036-10571") of an antibacterial component to be used as a pharmaceutical agent was dissolved in DMSO and adjusted and, as a negative control, DMSO was used.

The samples thus adjusted were immersed in the paper disc, disposed on an agar medium in which *bacillus subtilis* was seeded, cultured, and then, after 24 hours later, the measurement of the inhibition zone was performed. The results are shown in Table 4. The reliability of this example is confirmed from the size of the inhibition zone by chloramphenicol.

TABLE 4

Antibacterial activity by each compound

| | Added concentration (mM) | Diameter of inhibition zone (mm) |
|---|---|---|
| Resveratrol | 50 | 10.0 |
| | 10 | 0.0 |
| | 5 | 0.0 |
| | 1 | 0.0 |
| UHA 4002 | 50 | 16.0 |
| | 10 | 13.3 |
| | 5 | 11.0 |
| | 1 | 8.5 |
| UHA 4003 | 50 | 14.0 |
| | 10 | 11.8 |
| | 5 | 10.5 |
| | 1 | 8.3 |

From the results shown in Table 4, the UHA4002 and 4003 obtained inhibition zones of a sufficient size at a concentration lower than that of resveratrol. More specifically, it was shown that the UHA4002 and 4003 have much stronger antibacterial activity than that of resveratrol.

Example 6

Anticancer Action to Oral Cancer of Resveratrol Polymerization Compound

Next, in order to see the effect of the resveratrol polymerization compound to oral cancer cells, the cancer cell growth inhibitory action using SCC-4 cells (human oral cancer cells, ATCC) was tested.

For culturing of the SCC-4 cells, a DMEM/F-12 (1:1) culture medium (manufactured by GIBCO) containing 400 ng/mL hydrocortisone (manufactured by Sigma-Aldrich Japan), 1% antibiotic-antimycotic (manufactured by GIBCO), and 10% FBS (Fetal Bovine Serum, manufactured by ATCC) was used. For the test, a collagen I coat 96-well plate for cell culture (manufactured by Japan BD) was used, and SCC-4 cells whose number of cells was adjusted to be $5 \times 10^5$ cells/mL were seeded with 100 µL/well. The cells were cultured under the conditions of 37° C. and 5% $CO_2$ for 24 hours, and were used for the test in a confluent state of 80% or higher.

As the samples, resveratrol and the UHA4002 and 4003 which were purified were used. With respect to the sample preparation, each compound was dissolved with DMSO, and then prepared in such a manner as to be 0.63 mM, 1.25 mM, 2.5 mM, 5 mM, and 10 mM. The samples were added in such a manner that the final concentration in the SCC-4 cell culture solution was 6.3 µM, 12.5 µM, 25 µM, 50 µM, and 100 µM, and then the test was started. The sample to which an equivalent amount of only DMSO as the solvent was added was used as a negative control.

The number of viable cells was quantified by an MTT method using a "Cell counting kit-8" in the same manner as in Example 3, and the concentration $IC_{50}$ at which the cell growth is inhibited by 50% was calculated. The results are shown in Table 5. From these results, each resveratrol polymerization compound was recognized to have oral cancer cell growth inhibition ability higher than that of resveratrol as the raw material.

TABLE 5

| Compound name | Cell growth inhibition ability ($IC_{50}$, µM) |
|---|---|
| Resveratrol | >100 |
| UHA 4002 | 52.1 |
| UHA 4003 | 32.4 |

Example 7

Lipase Inhibitory Action of Resveratrol Polymerization Compound

In order to see the inhibitory action to lipase of the resveratrol polymerization compound, an inhibitory action test using rat intestine derived lipase was performed.

As lipase, one obtained by suspending 100 mg of rat derived intestine acetone powder (manufactured by Sigma-Aldrich Japan) in 1 mL of 100 mM citric acid buffer (pH 6.0), stirring the same at 4° C. for 1 hour, centrifuging the same (at 15000 rpm for 45 minutes at 4° C.) to obtain a supernatant, and then diluting the supernatant by 1500 times was used as a lipase solution.

As the samples, resveratrol and the UHA4002 which was already purified were used. With respect to the sample preparation, those obtained by dissolving each compound with DMSO, and then preparing in such a manner as to be 0.1 mM, 0.5 mM, 1 mM, 2 mM, and 4 mM were used.

For measuring the activity, a "Lipase kit S" (Trade name, manufactured by Dainippon Pharmaceutical Co., Ltd.) was used. First, in accordance with a preparation method described in the catalog of the Lipase kit S, a color developing liquid was prepared. Reaction liquids in which 70 µL, of the color developing liquid, 2 µL of an esterase inhibitor, 10 µL of the lipase solution, and 10 µL of the samples (Final concentration: 10 µM, 50 µM, 100 µM, 200 µM, 400 µM, and 1000 µM) were mixed were prepared, preincubated at 30° C. for 5 minutes, and then 8 µl of a substrate solution described in the catalog was added. Then, a reaction was started. After reacting for 10 minutes, 150 µL of a reaction stop liquid prepared in accordance with the preparation method described in the catalog of the Lipase kit S was added to stop the reaction. The resultant substance was subjected to absorbancy measurement at a wavelength of 415 nm. A reaction liquid to which only DMSO as the solvent of the sample was added was used as a positive control and one to which 10 μL of 100 mM citric acid buffer (pH 6.0) was added instead of the lipase solution was used as a negative control. From the relationship between the lipase inhibition rate calculated based on the data obtained therefrom and the concentration of each compound, the concentration $IC_{50}$ at which the lipase activity is inhibited by 50% was calculated. The results are shown in Table 6.

TABLE 6

| | Lipase inhibitory action ($IC_{50}$, μm) |
|---|---|
| Resveratrol | >1000 |
| UHA 4002 | 311.3 |

From these results, a lipase inhibition activity higher than that of the raw materials was observed in the resveratrol polymerization compound. Thus, the resveratrol polymerization compound demonstrates outstanding lipase inhibitory action, and therefore it is considered that the compound is useful as antiobesity agents and also as metabolic syndrome prevention agents. Moreover, since the lipase inhibition on the skin is effective for prevention of pimples and recovery from pimples, it is considered that the compound is useful also as skin disease therapeutic agents for prevention of pimples, recovery of pimples, and the like.

Example 8

Preparation of UHA4002 and 4003 Containing Solid

By a usual method of passing ethanol aqueous solutions in which the ethanol concentration was gradually increased for purification using a column charged with a synthetic adsorbent HP-20 (manufactured by Mitsubishi Chemical Corporation), 20 g resveratrol was obtained from 250 g of grape skin extract powder (manufactured by Marine Bio Co., Ltd.). 20 g of the obtained resveratrol was dissolved in 400 ml of ethanol, and then 400 ml of a 2.5% $NaHCO_3$ aqueous solution was added to obtain a resveratrol containing solution (pH 9.9). The resveratrol containing solution was heated at 130° C. for 20 minutes in an autoclave. Subsequently, 400 ml of ethanol and 400 ml of a 5.0% $NaHCO_3$ aqueous solution were added to the reaction solution obtained by the first autoclave treatment, and then heated again at 130° C. for 20 minutes in the autoclave. The finally obtained reaction solution was heated under reduced pressure to be dried and solidified, and then heated to reflux with ethanol. Then, insoluble matter contained in the obtained reaction mixture was removed by filtration. Thereafter, the filtrate was heated under reduced pressure to be dried and solidified to obtain 15 g of a solid. The content of the compound 1 and the compound 2 in the obtained solid (hereinafter referred to as "UHA4002 and 4003 containing solid") were 1.9 g and 0.9 g, respectively. This operation was repeated as required.

Example 9

Food Containing Resveratrol Polymerization Compound 10 g of the UHA4002 and 4003 containing solid obtained in Example 6 was dissolved in 100 mL of ethanol beforehand, 500 g of sugar and 400 g of starch syrup were mixed and dissolved in the solution, and then 100 g of fresh cream, 20 g of butter, 70 g of condensed milk, and 1.0 g of an emulsifier were mixed with the mixture. Then, the pressure was reduced to −550 mmHg in a vacuum pan, and then the resultant mixture was condensed under the condition of 115° C., thereby obtaining a milk hard candy having a moisture value of 3.0% by weight. It is a matter of course that this article is easy to eat as a confectionery and this article can be also utilized as a health function food which is expected to achieve curing and prevention of infectious diseases, curing and prevention of cancer, curing and prevention of lifestyle-related diseases, and beauty effects.

Example 10

Preparation of UHA4002, 4003

20 g of resveratrol (manufactured by Tokyo Chemical Industry Co., Ltd.) was dissolved in 400 ml of ethanol, and then 400 ml of a 2.5% $NaHCO_3$ aqueous solution was added thereto to obtain a resveratrol containing solution (pH 9.9). The resveratrol containing solution was heated at 130° C. for 20 minutes in an autoclave. Subsequently, 400 ml of ethanol and 400 ml of a 5.0% $NaHCO_3$ aqueous solution were added to the reaction solution obtained by the first autoclave treatment, and then heated again at 130° C. for 20 minutes in the autoclave. The finally obtained reaction solution was heated under reduced pressure to be dried and solidified, and then heated to reflux with ethanol. Then, insoluble matter contained in the obtained reaction mixture was removed by filtration. Thereafter, the filtrate was heated under reduced pressure to be dried and solidified to obtain 15 g of a solid. Subsequently, UHA4002 and 4003 were purified from the solid using fractionation HPLC (column: ODS C18). 1.6 g of the compound 1 was obtained and 0.8 g of the compound 2 was obtained. This operation was repeated as required.

Example 11

Pharmaceutical Agent Containing Resveratrol Polymerization Compound

The UHA4002 obtained by the method of Example 8 was dissolved in ethanol, adsorbed to microcrystalline cellulose, and then dried under reduced pressure. From the resultant substance, a tablet product was obtained according to a usual method. The formula is as follows: 10 parts by weight of UHA4002, 23 parts by weight of cornstarch, 12 parts by weight of milk sugar, 8 parts by weight of carboxymethyl cellulose, 32 parts by weight of microcrystalline cellulose, 4 parts by weight of polyvinyl pyrrolidone, 3 parts by weight of magnesium stearate, and 8 parts by weight of talc. The tablet product can be effectively used as a pharmaceutical agent aiming at recovery from infectious diseases, recovery from cancers, and recovery from lifestyle-related diseases and further a pharmaceutical agent aiming at beauty effects.

Example 12

Quasi Drug Containing Resveratrol Polymerization Compound 1 g of the UHA4002 and 0.2 g of the UHA4003 obtained by the method of Example 8 were dissolved in 10 mL of ethanol, 20 g of taurine, 0.12 g of vitamin B1 nitrate, 0.6 g of sodium benzoate, 4 g of citric acid, 60 g of sugar, and 10 g of polyvinyl pyrrolidone were all dissolved in purified water, and then the solution was diluted in a measuring cylinder to 1000 ml. The pH was adjusted to 3.2 using dilute hydrochloric acid.

50 ml of 1000 ml of the obtained solution was charged into a glass bottle, and then sterilized at 80° C. for 30 minutes, thereby completing a drink agent which is a quasi drug. The drink agent can be effectively utilized as a quasi drug aiming at reducing the risk of infectious diseases in addition to the purpose of supply of nutrients.

Example 13

Cosmetics Containing Resveratrol Polymerization Compound 1 part by weight of polyoxyethylene sorbitol tetraoleate, 0.5 part by weight of polyoxyethylene stearyl ether, 1 part by weight of lipophilic glyceryl monostearate, 0.5 part by weight of pyruvic acid, 0.5 part by weight of stearyl alcohol, 1 part by weight of avocado oil, and 0.1 part by weight of the UHA4002 obtained by the method of Example 8 were dissolved according to a usual method, 1 part by weight of sodium lactate, 5 parts by weight of propylene glycol, 0.1 part by weight of carboxy vinyl polymer, a very slight amount of spice, and 89.3 parts by weight of purified water were added thereto, and the mixture was treated by a homogenizer for emulsification, thereby obtaining a milky lotion. The milky lotion can be effectively used as a medicated cosmetic with a skin infectious disease preventive effect not only as cosmetics with skin enhancement and the sunscreen effect.

The invention claimed is:

1. A resveratrol polymerization compound represented by Formula (1):

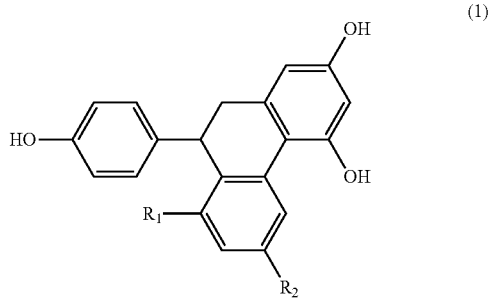

wherein, in Formula (1), $R_1$ and $R_2$ independently represent —OH or Formula (2):

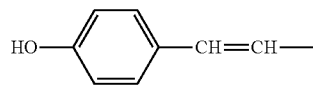

and $R_1$ and $R_2$ are not the same, or a pharmaceutically acceptable salt thereof.

2. An agent for the treatment of cancer comprising at least one compound selected from the group consisting of the resveratrol polymerization compound and the pharmaceutically acceptable salt thereof according to claim 1.

3. An antioxidant comprising at least one compound selected from the group consisting of the resveratrol polymerization compound and the pharmaceutically acceptable salt thereof according to claim 1.

4. An antibacterial agent comprising at least one compound selected from the group consisting of the resveratrol polymerization compound and the pharmaceutically acceptable salt thereof according to claim 1.

5. A lipase inhibitor comprising at least one compound selected from the group consisting of the resveratrol polymerization compound and the pharmaceutically acceptable salt thereof according to claim 1.

6. An antiobesity agent comprising at least one compound selected from the group consisting of the resveratrol polymerization compound and the pharmaceutically acceptable salt thereof according to claim 1.

7. A food, a pharmaceutical agent, or a cosmetic comprising at least one compound selected from the group consisting of the resveratrol polymerization compound and the pharmaceutically acceptable salt thereof according to claim 1.

8. A method for manufacturing the resveratrol polymerization compound or the pharmaceutically acceptable salt thereof according to claim 1 comprising:
heat treating resveratrol under alkaline conditions.

9. A method for manufacturing the resveratrol polymerization compound or the pharmaceutically acceptable salt thereof according to claim 8, wherein:
the heat treating is performed in a resveratrol-containing solution with a pH of at least 8.0.

* * * * *